US012478751B2

(12) United States Patent
Gong et al.

(10) Patent No.: US 12,478,751 B2
(45) Date of Patent: Nov. 25, 2025

(54) POSITIVE AIRWAY PRESSURE (PAP) MASK

(71) Applicant: Sleepnet Corporation, Hampton, NH (US)

(72) Inventors: Mark Gong, Andover, MA (US); Jerry Gong, Andover, MA (US); Robert Skaff, Hampton, NH (US); Thomas Moulton, Rye, NH (US)

(73) Assignee: Sleepnet Corporation, Hampton, NH (US)

( * ) Notice: Subject to any disclaimer, the term of this patent is extended or adjusted under 35 U.S.C. 154(b) by 685 days.

(21) Appl. No.: 17/864,644

(22) Filed: Jul. 14, 2022

(65) Prior Publication Data

US 2022/0395662 A1 Dec. 15, 2022

Related U.S. Application Data

(62) Division of application No. 17/347,717, filed on Jun. 15, 2021, now Pat. No. 11,529,485.

(51) Int. Cl.
*A61M 16/06* (2006.01)
*A61M 16/08* (2006.01)

(52) U.S. Cl.
CPC .... *A61M 16/0622* (2014.02); *A61M 16/0825* (2014.02); *A61M 2205/02* (2013.01)

(58) Field of Classification Search
CPC ................ A61M 16/024; A61M 16/06; A61M 16/0605; A61M 16/0611; A61M 16/0616;
(Continued)

(56) References Cited

U.S. PATENT DOCUMENTS 4,603,692 A * 8/1986 Montesi ............... A62B 18/084 128/207.11
6,019,101 A 2/2000 Cotner et al.
(Continued)

FOREIGN PATENT DOCUMENTS

EP 2818194 A1 12/2014
WO 2007045023 A1 4/2007
WO 2008037031 A1 4/2008

OTHER PUBLICATIONS

International Search Report and the Written Opinion of the International Searching Authority for International Application No. PCCT/US2022/033400 mailed Oct. 20, 2022, 11 pages.
(Continued)

*Primary Examiner* — Annette Dixon
(74) *Attorney, Agent, or Firm* — Pierce Atwood LLP; Christopher A. Baxter

(57) ABSTRACT

A flexible positive airway pressure (PAP) mask body, frame, and cushion are described. The mask body includes prongs that insert through and act upon apertures of the mask frame to connect the mask frame to the mask body. An airtight seal may be created between the mask body and the mask frame by a ball and socket connector, of the mask frame, having an elongated portion that extends through and has an outer perimeter commensurate with an aperture located in the mask body. The mask body may be configured with elongated portions that extend from the mask body chamber and to ends of eye sockets of the user. Headgear may couple to end portions of the mask frame corresponding to the elongated portions of the mask body. When pulling pressure by the headgear, additional contact is created between elongated portions of the mask cushion and the user's face.

14 Claims, 5 Drawing Sheets

(58) Field of Classification Search

CPC .......... A61M 16/0622; A61M 16/0633; A61M 16/0644; A61M 16/0683; A61M 16/0816; A61M 16/0825; A61M 16/085; A61M 16/0875; A61M 16/208; A61M 2016/0661; A61M 2039/2426; A61M 2202/0014; A61M 2202/0085; A61M 2202/0208; A61M 2202/0225; A61M 2205/42; A61M 2210/0618; A61M 2230/432; A61M 2240/00; A62B 18/084

See application file for complete search history.

(56) References Cited

U.S. PATENT DOCUMENTS

| | | | | |
|---|---|---|---|---|
| 6,119,694 | A | 9/2000 | Correa et al. | |
| 6,631,718 | B1 | 10/2003 | Lovell | |
| 7,845,352 | B2 | 12/2010 | Sleeper et al. | |
| 7,938,117 | B2 | 5/2011 | Chiesa et al. | |
| 9,308,343 | B2 | 4/2016 | Groll et al. | |
| 9,669,176 | B2 | 6/2017 | Sullivan et al. | |
| 10,034,994 | B2 * | 7/2018 | McAuley | A61M 16/0622 |
| 10,974,007 | B2 | 4/2021 | Moulton et al. | |
| 2005/0051171 | A1 | 3/2005 | Booth | |
| 2006/0060200 | A1 | 3/2006 | Ho et al. | |
| 2006/0196510 | A1 * | 9/2006 | McDonald | A61M 16/06 128/205.25 |
| 2007/0209663 | A1 | 9/2007 | Marque et al. | |
| 2010/0126504 | A1 | 5/2010 | Johnstone | |
| 2010/0192954 | A1 | 8/2010 | Sullivan et al. | |
| 2010/0313891 | A1 * | 12/2010 | Veliss | A61M 16/06 128/206.26 |
| 2012/0138061 | A1 * | 6/2012 | Dravitzki | A61M 16/0683 128/205.25 |
| 2014/0166007 | A1 | 6/2014 | Bordewick et al. | |
| 2019/0275279 | A1 | 9/2019 | Giudice et al. | |
| 2020/0197649 | A1 | 6/2020 | Haibach | |
| 2022/0096769 | A1 | 3/2022 | Guney et al. | |

OTHER PUBLICATIONS

European Search Report, Application No. 22825653.3, Sleepnet Corporation, Feb. 21, 2025.

* cited by examiner

POSITIVE AIRWAY PRESSURE (PAP) MASK

BACKGROUND

Hospital and at home patents sometimes need supplemental respiratory support. Positive pressure ventilation, in which a supply of pressurized air is delivered to the patient's airway, is often used. Positive pressure ventilation has been used to treat respiratory failure, respiratory insufficiency, and sleep apnea. There are a variety of patient interfaces which can be used to provide positive pressure ventilation including Nasal masks, Full Face masks, and Nasal Pillows for home and hospital use.

PAP, or positive airway pressure, is a treatment that uses air pressure to keep the airways open. PAP treatment typically is used by people who have breathing problems, such as sleep apnea. Sleep disorder breathing is a common disorder that causes pauses in breathing or shallow breaths while a person sleeps. As a result, not enough air reaches the person's lungs.

In obstructive sleep apnea, the person's airway collapses or is blocked during sleep. Air pressure from PAP treatment can prevent that person's airway from collapsing or becoming blocked.

PAP treatment basically involves: a PAP machine that blows therapeutic air; and a PAP mask assembly that receives the therapeutic air from the machine via an interconnecting hose. PAP mask assemblies typically comprise a mask body of rigid or pliable material (e.g., plastic) with a face-contacting cushion (e.g., a gel filled bladder) that is held in place with headgear (e.g., straps). The mask body provides the structure for: a headgear connector; straps that can be removably attached to the headgear connector; and a swiveling elbow assembly to which the hose can be attached. The cushion provides a seal against the patient's face, creating a chamber around the airway through which positive pressure ventilation can be applied.

SUMMARY

An aspect of the present disclosure relates to a positive airway pressure (PAP) mask assembly including a mask body, a mask frame, and a mask cushion. The mask body is formed from a flexible material. The mask body includes a convex surface and a first prong and a second prong each extending outwardly from the convex surface. The mask frame includes a concave surface including a first aperture and a second aperture located therein. The mask cushion is coupled to the mask body, and includes a gel. The first prong and the second prong are configured to act upon the first aperture and the second aperture, respectively, to removably connect the mask body to the mask frame.

In at least some embodiments, the mask frame further includes a ball and socket connector configured to receive a ball portion of an end of an air tube. In at least some embodiments, the mask body further includes a third aperture in the convex surface thereof, the mask frame further includes an extension element extending from the concave surface thereof, and the extension element is configured to be inserted through and provide an airtight seal with the third aperture of the mask body when the first prong and the second prong act upon the first aperture and the second aperture, respectively. In at least some embodiments, a distance between the first prong and second prong is reduced when a force is applied to the convex surface of the mask body, and the first prong and the second prong are configured to be inserted through the first aperture and the second aperture, respectively, when the distance is reduced. In at least some embodiments, the mask frame further includes a convex surface, and the first prong and the second prong are configured to be inserted through the first aperture and the second aperture, respectively, when a force is applied to the convex surface of the mask frame. In at least some embodiments, a distance between the first aperture and the second aperture is increased when the force is applied to the convex surface of the mask frame. In at least some embodiments, the mask body is configured to fit over at least a portion of a nose of a user. In at least some embodiments, the mask body is configured to fit over a mouth and at least a portion of a nose of a user. In at least some embodiments, the mask body further includes a retaining element molded therein, the retaining element being configured to reshape and retain the convex surface of the mask body to features of a face of a user. In at least some embodiments, the flexible material of the mask body is a malleable plastic. In at least some embodiments, the malleable plastic is polyvinyl chloride.

Another aspect of the present disclosure relates to a mask frame of PAP mask assembly, where the mask frame includes a concave surface, a first aperture within the concave surface, and a second aperture within the concave surface. The first aperture is configured to receive a first prong extending from a convex surface of a mask body. The second aperture is configured to receive a second prong extending from the convex surface of the mask body. The mask frame is configured to removably connect to the mask body when the first aperture and the second aperture are acted upon by the first prong and the second prong, respectively.

In at least some embodiments, the mask frame further includes a ball and socket connector configured to receive a ball portion of an end of an air tube. In at least some embodiments, the mask frame further includes an extension element configured to be inserted through and provide an airtight seal with a third aperture of the mask body when the first aperture and the second aperture are acted upon by the first prong and the second prong, respectively. In at least some embodiments, the mask frame further includes a convex surface, and the first aperture and the second aperture are configured to receive the first prong and the second prong, respectively, when a force is applied to the convex surface of the mask frame. In at least some embodiments, a distance between the first aperture and the second aperture is increased when the force is applied to the convex surface. In at least some embodiments, the mask frame is constructed using a thermoplastic polymer. In at least some embodiments, the thermoplastic polymer is polypropylene. In at least some embodiments, the mask frame is constructed using polyvinyl chloride. In at least some embodiments, the mask frame is constructed using acrylonitrile-butadiene-styrene. In at least some embodiments, the mask frame is constructed using at least one malleable metal.

A further aspect of the present disclosure relates to a PAP mask body include a chamber defined by a flexible material and configured to be placed over at least a portion of a nose of a user, a first elongated portion comprising the flexible material and extending from the chamber and toward a first cheek of the user, a second elongated portion comprising the flexible material and extending from the chamber and toward a second check of the user, and a cushion attachment surface surrounding the chamber and extending along the first elongated portion and the second elongated portion. The flexible material enables the first elongated portion to be folded toward the second elongated portion without causing a lower portion of the chamber to deform.

In at least some embodiments, the PAP mask body further includes a retaining element molded into the flexible material defining the chamber, where the retaining element is configured to reshape and retain the flexible material to features of a face of the user. In at least some embodiments, the cushion attachment surface is configured to contact a portion of the nose of the user below a bridge of the nose. In at least some embodiments, the chamber has a first height and the first elongated portion has a second height, where the second height is less than the first height. In at least some embodiments, the second height is about 50% to about 99% of the first height. In at least some embodiments, the second height is about 80% of the first height. In at least some embodiments, the chamber has a first width and the first elongated portion has a second width, where the second width is about one-third to about one-half of the first width. In at least some embodiments, the flexible material is a malleable plastic. In at least some embodiments, the malleable plastic is polyvinyl chloride.

BRIEF DESCRIPTION OF DRAWINGS

For a more complete understanding of the present disclosure, reference is now made to the following description taken in conjunction with the accompanying drawings.

DETAILED DESCRIPTION

Figures 1A, 1B, 1C, 1D:
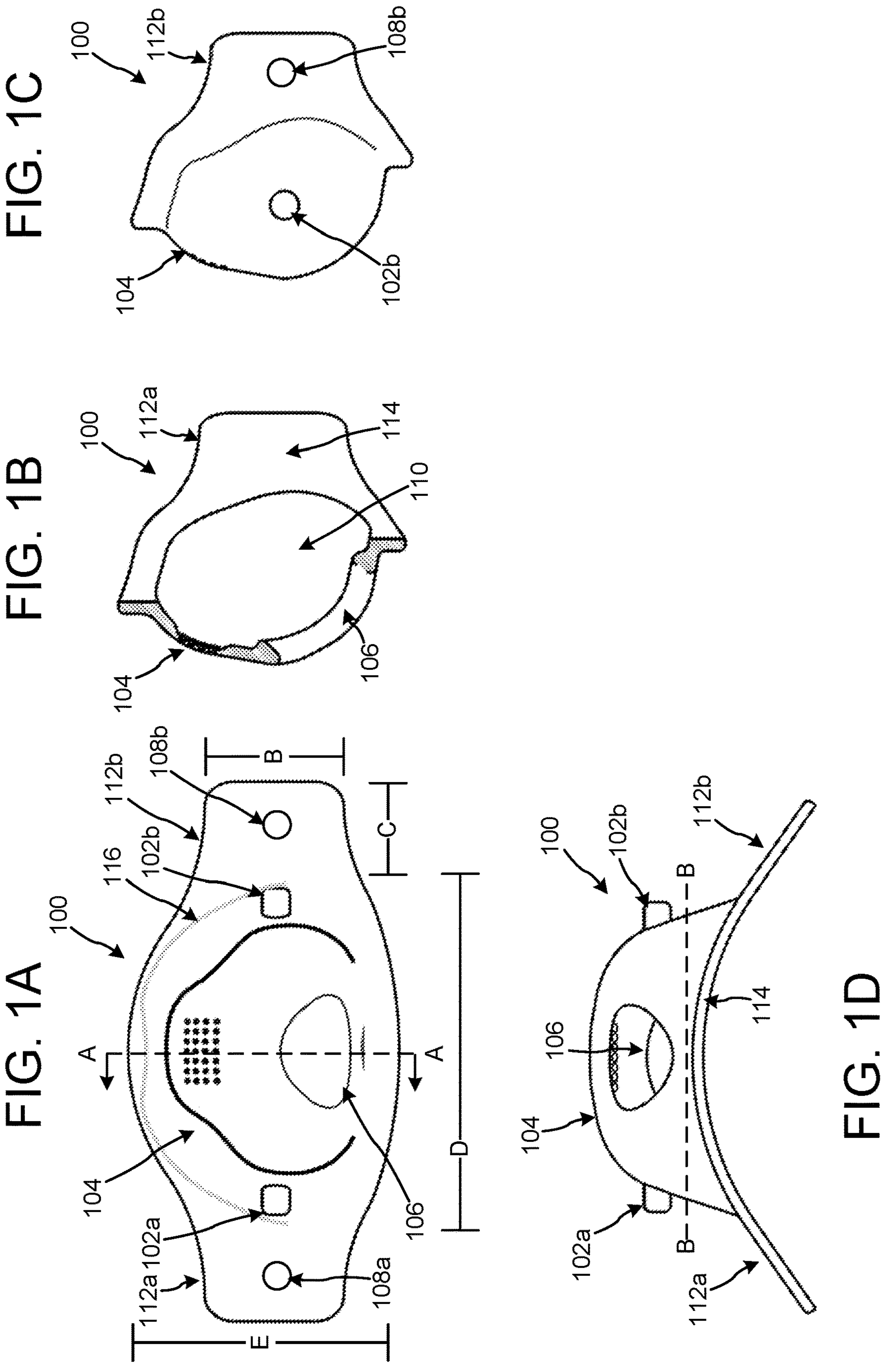
FIG. 1A is a front view of a mask body, according to embodiments of the present disclosure.
FIG. 1B is a cross-sectional view of the mask body of FIG. 1A taken along line A-A, according to embodiments of the present disclosure.
FIG. 1C is a left-side view of the mask body of FIG. 1A, according to embodiments of the present disclosure.
FIG. 1D is a bottom view of the mask body of FIG. 1A, according to embodiments of the present disclosure.

The present disclosure provides a flexible positive airway pressure (PAP) mask body configured to accommodate variations in facial structures and geometries of different users. The mask body of the present disclosure is configured such that a user may adjust and shape the mask body to fit the user's facial contours without relying on excess force and pressure from tightening of headgear.

Some facial geometries may require using a combination of shaping and headgear tightening to create a seal against a user's face. In some embodiments, the flexible mask body of the present disclosure may be affixed to a mask cushion, including a soft, malleable material such as a gel, that conforms to a user's facial features to create an airtight seal without excess pressure from tightening of headgear.

The mask body includes prongs that extend from a convex surface thereof. The prongs are configured to insert through apertures of an arcuate mask frame, where the mask frame may have a convexity corresponding to a convexity of the mask body. The prongs act upon the apertures of the mask frame to connect the mask frame to the mask body. However, in at least some embodiments such connection may not provide an airtight seal between the mask body and the mask frame. In such embodiments, the airtight seal may be provided by a ball and socket connector, of the mask frame, having an elongated portion that extends through and has an outer perimeter commensurate with an aperture located in the mask body.

In at least some embodiments, the mask body is configured with elongated portions (or wings) configured to extend from the chamber of the mask body, toward cheeks of a user, and to ends of eye sockets of the user. Headgear may couple to end portions of the mask frame corresponding to the elongated portions of the mask body. When pulling pressure is applied to the mask frame by the headgear, additional contact is created between elongated portions of the mask cushion and the user's face, resulting in an improved airtight seal.

Further details of the foregoing mask body, mask frame, and mask cushion, as well as a mask assembly including same, are described below.

Mask Body

FIGS. 1A-1D illustrate an example mask body 100 of the present disclosure. In some embodiments, the mask body 100 may be configured to fit over at least a portion of a nose (e.g., at least nostrils) of a user. Such may be referred to as a nasal mask body. In some other embodiments, the mask body 100 may be configured to fit over a mouth and at least a portion of a nose of a user. Such may be referred to as an oronasal mask body. In some embodiments, the mask body 100 may be low-profile, meaning the mask body 100 may fit over at least a portion of the user's nose, but not extend all the way up to the bridge of the user's nose. Such a mask body 100 may be more trapezoidal than triangular.

The mask body 100 includes a concave surface 110 defining a chamber. The dimensions of the concave surface 110, and thus the volume of the chamber, is configurable based on nose heights of users and/or air volume requirements for proper PAP use. The mask body 100 includes a convex surface 104 corresponding to the concave surface 110.

The mask body 100 includes an aperture 106 located through the convex surface 104 and the concave surface 110. The aperture 106 may be configured to receive and create an airtight seal with a portion of a mask frame 200 (described in detail herein with respect to FIGS. 2A-2D). The size, shape, and placement of the aperture 106 is not limited to that illustrated in FIGS. 1A-1B and 1D. The size, shape, and placement of the aperture are configurable, provided that the aperture 106 may receive and create an airtight seal with a portion of the mask frame 200.

The convex surface 104 may also include a plurality of prongs (e.g., a first prong 102*a* and a second prong 102*b*) extending outwardly from the convex surface 104. The size, shape, and placement of the first prong 102*a* on the convex surface 104 are configurable. In some embodiments, as illustrated in FIGS. 1A and 1D, the first prong 102*a* may be cylindrical. That is, the first prong 102*a* may be an elongated structure having a circular cross-section. Moreover, as illustrated in FIG. 1D, in some embodiments the first prong 102*a* may be configured to extend parallel to a plane B-B of the mask body 100.

Like the first prong 102*a*, the size, shape, and placement of the second prong 102*b* on the convex surface 104 are configurable. In some embodiments, as illustrated in FIGS. 1A and 1C-1D, the second prong 102*b* may be cylindrical. That is, the second prong 102*b* may be an elongated structure having a circular cross-section. Moreover, as illustrated in FIG. 1D, in some embodiments the second prong 102*b* may be configured to extend parallel to the plane B-B of the mask body 100.

In some embodiments, the mask body 100 may include a retaining element 116 (e.g., a wire) configured to enable a user of the mask body 100 to form the convex surface 104 and the concave surface 110, and thus the chamber of the mask body 100, to features/contours of the user's face, thereby enabling a better seal of the mask body 100 to the user's face. In some embodiments, the mask body 100 may not include the retaining element 116. For example, in pediatric applications a sufficient seal may be provided via tension applied on the mask body 100 by headgear.

In some embodiments, the retaining element 116 may be disposed within the mask body 100 between the convex surface 104 and the concave surface 110. In other embodiments, the retaining element 116 may be affixed to the convex surface 104. In still other embodiments, the retaining element 116 may be affixed to the concave surface 110.

In embodiments where the mask body 100 is configured to surround a mouth of a user, the retaining element 116 may include a portion configured to be positioned along a chin of the user. In some embodiments, this portion of the retaining element 116 may be stiffened. For example, the foregoing portion of the retaining element 116 may be stiffened by molding a polycarbonate sleeve over the portion of the retaining element 116 before the retaining element 116, and polycarbonate sleeve, are molded in or affixed to the mask body 100. Stiffening of this portion of the retaining element 116 causes the portion to become more difficult to bend but not to be rigid (i.e., to be stiffened, compared to the remainder of the retaining element 116).

It is noted that there are a number of means known to those skilled in the art to stiffen the aforementioned portion of the retaining element 116. A polycarbonate overmold is one of the least costly and most esthetically attractive. It is also noted that the portion of the retaining element 116 that is stiffened may nonetheless still have some "give" in it.

The retaining element 116 can be constructed from any suitable material that is malleable and is capable of retaining a shape into which it is formed. In some embodiments, the retaining element 116 may be constructed from one or more malleable metals wires or strips. In some embodiments, the retaining element 116 may be constructed using one or more stainless steel wires or strips. In some embodiments, the retaining element 116 may be constructed from one or more non-metal materials, such as polypropylene or some other non-metal material that is capable of retaining its shape as it is bent.

The mask body 100 may be configured with a first elongated portion 112*a* and a second elongated portion 112*b*. The first elongated portion 112*a* may have a width sufficient to enable the first elongated portion 112*a* to extend from the convex surface 104/chamber of the mask body 100, toward a right cheek of a user, and to an end of a right eye socket of the user. Likewise, the second elongated portion 112*b* may have a width sufficient to enable the second elongated portion 112*b* to extend from the convex surface 104/chamber of the mask body 100, toward a left cheek of a user, and to an end of a left eye socket of the user. By configuring the first elongated portion 112*a* and the second elongated portion 112*b* to extend to the ends of the right and left eye sockets of a user, respectively, headgear (not illustrated) of the mask may operate on and apply pressure to the first elongated portion 112*a* and the second elongated portion 112*b* to create an airtight seal between a mask cushion 300 (described herein with respect to FIGS. 3A-3C), affixed to the mask body 100, and the user's face.

The first elongated portion 112*a* and the second elongated portion 112*b* may be configured to have the same width, although the first elongated portion 112*a* and the second elongated portion 112*b* need not be configured to have the same width. In some embodiments, one or both of the first elongated portion 112*a* and the second elongated portion 112*b* may have a width C that is about one-third (⅓) to about one-half (½) of a width D of the chamber of the mask body 100.

Likewise, the first elongated portion 112*a* and the second elongated portion 112*b* may be configured to have the same height, although the first elongated portion 112*a* and the second elongated portion 112*b* need not be configured to have the same height. In some embodiments, one or both of the first elongated portion 112*a* and the second elongated portion 112*b* may have a height B that is less than a height E of the chamber of the mask body 100. In some embodiments, the height B may be about 50% to about 99% of the height E. In some embodiments, the height B may be about 80% of the height E. Such height configurations may be beneficial in allowing headgear of the mask to operate on and apply pressure to the first elongated portion 112*a* and the second elongated portion 112*b* to create an airtight seal between a mask cushion 300 (described herein with respect to FIGS. 3A-3C), affixed to the mask body 100, and the user's face.

In at least some embodiments, one or both of the first elongated portion 112*a* and the second elongated portion 112*b* may have a magnet 108 molded therein or affixed thereto. For example, the first elongated portion 112*a* may have a first magnet 108*a* molded therein or affixed thereto and/or the second elongated portion 112*b* may have a second magnet 108*b* molded therein or affixed thereto. The magnet(s) 108 may be configured to attract a magnet(s) 214 of the mask frame 200 for the purpose of aligning the mask body 100 with the mask frame 200. But, in at least some embodiments, the magnet(s) 108 of the mask body 100 and the magnet(s) 214 of the mask frame 200 may not, in and of themselves, provide sufficient attractive forces to create an airtight seal between the mask body 100 and the mask frame 200.

The size, shape, and placement of the first magnet 108*a* in or on the first elongated portion 112*a* are configurable, provided that the first magnet 108*a* is capable of interacting with (i.e., through attractive magnetic forces) a first magnet

214*a* of the mask frame 200 to align the mask frame 200 with the mask body 100. Likewise, the size, shape, and placement of the second magnet 108*b* in or on the second elongated portion 112*b* are configurable, provided that the second magnet 108*b* is capable of interacting with (i.e., through attractive magnetic forces) a second magnet 214*b* of the mask frame 200 to align the mask frame 200 with the mask body 100.

The mask body 100 additionally includes a cushion attachment surface 114 configured to have a mask cushion 300 affixed thereto. Details of the mask cushion 300 are described herein below with respect to FIGS. 3A-3C. In at least some embodiments, a horizontal cross-section of the mask body 100, that runs parallel to the cushion attachment surface 114, may be trapezoidal. The z-axis of the mask body 100, that runs from the cushion attachment surface 114 to the concave surface 110, may be a flattened dome shape, except the base of the flattened dome is a trapezoid instead of a circle. The z-axis (e.g., height) of the mask body 100 is configured to accommodate the nose of the user and provide a chamber volume sufficient enough for fresh air (inserted into the chamber by a PAP machine) and exhaled air of the user to mix.

In at least some embodiments, the mask body 100 may be formed from a flexible material. More specifically, in at least some embodiments the concave surface 110, the convex surface 104, the first prong 102*a*, the second prong 102*b*, the first elongated portion 112*a*, and the second elongated portion 112*b* may all be formed from the same flexible material. In some embodiments, the flexible material may be a malleable plastic. In some embodiments, the malleable plastic may be polyvinyl chloride (PVC).

Mask Frame

FIGS. 2A-2D illustrate an example mask frame 200 of the present disclosure. The mask frame 200 includes a convex surface 206 and a concave surface 208. In at least some embodiments, the concave surface 208 may have a concavity commensurate with a convexity of the convex surface 104 of the mask body 100.

The mask frame 200 may include a plurality of apertures (e.g., a first aperture 204*a* and a second aperture 204*b*) within the convex surface 206 and the concave surface 208. The first aperture 204*a* may be configured to receive the first prong 102*a* of the mask body 100. Likewise, the second aperture 204*b* may be configured to receive the second prong 102*b* of the mask body 100. The first prong 102*a* and the second prong 102*b* may act upon the first aperture 204*a* and the second aperture 204, respectively, to removably connect the mask frame 200 to the mask body 100.

In some embodiments, the first aperture 204*a* and the second aperture 204*b* may be elongate, in the form of slots, as illustrated in FIGS. 2A-2D. However, the size, shape, and placement of the first aperture 204*a* and the second aperture 204*b* in the mask frame 200 is not limited thereto. It is noted that the size, shape, and placement of the first aperture 204*a* and the second aperture 204*b* are configurable, provided that the first aperture 204*a* and the second aperture 204*b* are configured to receive the first prong 102*a* and the second prong 102*b* of the mask body 100, respectively. For example, in some embodiments the first aperture 204*a* and the second aperture 204*b* may be shaped to be commensurate with a shape of the first prong 102*a* and the second prong 102*b*, respectively. For example, if the first prong 102*a* and the second prong 102*b* are cylindrical, the first aperture 204*a* and the second aperture 204*b* may be circular.

In some embodiments, instead of being configured with the first aperture 204*a* and the second aperture 204*b*, the mask frame 200 may include a first indentation and a second indentation in the concave surface 208 of the mask frame 200, an optionally a corresponding first protrusion and second protrusion extending from the convex surface 206. In such embodiments, the first indentation and the second indentation may be configured to receive and be acted upon by the first prong 102*a* and the second prong 102*b*, respectively, to connect the mask frame 200 to the mask body 100.

Figures 2A, 2B, 2C, 2D:
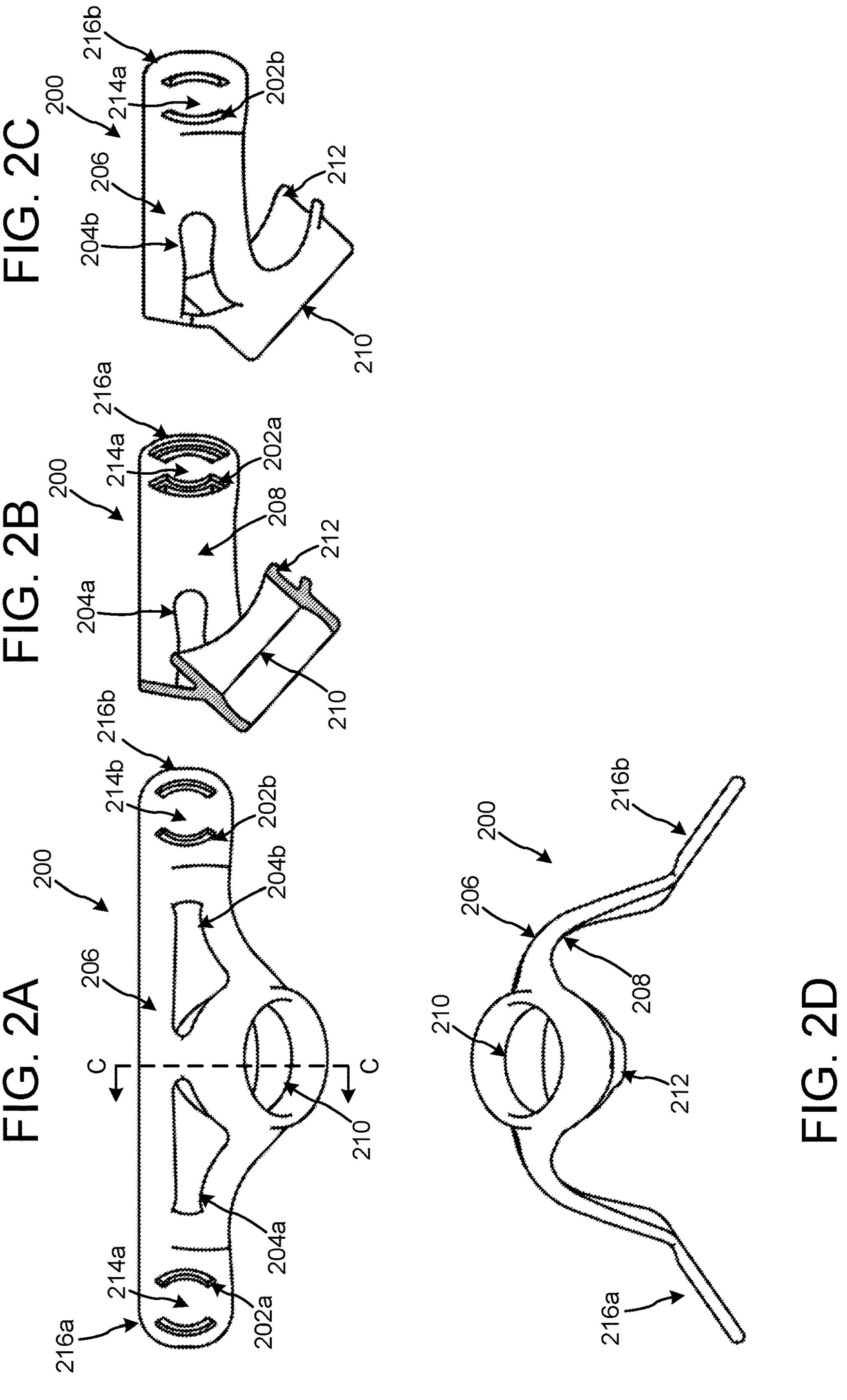
FIG. 2A is a front view of a mask frame, according to embodiments of the present disclosure.
FIG. 2B is a cross-sectional view of the mask frame of FIG. 2A taken along line C-C, according to embodiments of the present disclosure.
FIG. 2C is a right-side view of the mask frame of FIG. 2A, according to embodiments of the present disclosure.
FIG. 2D is a bottom view of the mask frame of FIG. 2A, according to embodiments of the present disclosure.

The mask frame 200 includes a first end portion 216*a* and a second end portion 216*b*. As illustrated in FIG. 2D, the first end portion 216*a* and the second end portion 216*b* may be angularly offset from the convex surface 206. In at least some embodiments, one or both of the first end portion 216*a* and the second end portion 216*b* may have a magnet 214 located therein or affixed thereto. For example, the first end portion 216*a* may have a first magnet 214*a* located therein or affixed thereto and/or the second end portion 216*b* may have a second magnet 214*b* located therein or affixed thereto. The magnet(s) 214 may be configured to attract a magnet(s) 108 of the mask body 100 for the purpose of aligning the mask body 100 with the mask frame 200. But, in at least some embodiments, the magnet(s) 214 of the mask frame 200 and the magnet(s) 108 of the mask body 100 may not, in and of themselves, provide sufficient attractive forces to create an airtight seal between the mask body 100 and the mask frame 200. The first magnet 214*a* and the second magnet 214*b* may additionally or alternatively be configured to attract corresponding magnets of headgear, such that a user can locate where the headgear is to attached to the mask frame 200 (e.g., if the user need to disconnect the headgear from the mask frame 200 in the middle of the night and thereafter reattach same).

The size, shape, and placement of the first magnet 214*a* in or on the first end portion 216*a* are configurable, provided that the first magnet 214*a* is capable of interacting with (i.e., through attractive magnetic forces) a first magnet 108*a* of the mask body 100. Likewise, the size, shape, and placement of the second magnet 214*b* in or on the second end portion 216*b* are configurable, provided that the second magnet 214*b* is capable of interacting with (i.e., through attractive magnetic forces) a second magnet 108*b* of the mask body 100. Interaction of the first magnets 108*a*/214*a* and the second magnets 108*b*/214*b* may align the mask body 100 with the mask frame 200 such that the first aperture 204*a* may be aligned to receive the first prong 102*a* of the mask body 100, and the second aperture 204*b* may be aligned to receive the second prong 102*b* of the mask body 100.

The mask frame 200 may be configured to connect to headgear for holding the mask body 100 against a face of a user. In at least some embodiments, the first end portion 216*a* may include a first headgear attachment portion 202*a* (represented by the two arcuate apertures in FIGS. 2A-2B), and the second end portion 216*b* may include a second headgear attachment portion 202*b* (represented by the two arcuate apertures in FIGS. 2A and 2C).

It is noted that there are various art-known/industry-known headgear, any of which may be used with the PAP mask of the present disclosure. It thus follows that the first headgear attachment portion 202*a* and the second headgear attachment portion 202*b* may be configured to connect to one or more art-known/industry-known headgear. Notwithstanding, the first headgear attachment portion 202*a* and the second headgear attachment portion 202*b* may be configured to connected to proprietary headgear, in at least some embodiments.

The mask frame 200 is configured to receive and connect to a tube configured to provide pressurized air. In at least some embodiments, the mask frame 200 may include a ball and socket connector 210 configured to receive and provide an airtight seal with the tube. The ball and socket connector 210 is a coupling mechanism that includes a spherical socket configured to receive a corresponding spherical end of the tube. In some embodiments, the end of the tube may be semi-spherical but nonetheless capable of providing an airtight seal with the walls of the spherical socket of the ball and socket connector 210. A spherical end of a tube and a semi-spherical end of a tube may each be referred to as a ball portion of a tube herein. The spherical nature of the ball and socket connector 210, combined with the spherical (or semi-spherical) end of the tube, allows for multidirectional movement and rotation of the tube within the ball and socket connector 210. Such multidirectional movement permits a user to sleep at different positions with respect to the compressor/motor of the PAP without experiencing tube drag, or with experiencing less tube drag then industry-known PAP configurations.

In at least some embodiments, the mask frame 200 may include an extension element 212 that extends from the end of the ball and socket connector 210 corresponding to the concave surface 208 of the mask frame 200. The extension element 212 may be configured to be inserted through the aperture 106 of the mask body 100 when the mask body 100 is connected to the mask frame 200. In at least some embodiments, operation of the first prong 102*a* and the second prong 102*b* upon the first aperture 204*a* and the second aperture 204*b* of the mask frame 200, respectively, may physically connect the mask frame 200 to the mask body 100, but an airtight seal between the mask frame 200 (and more particularly the tube connected to the ball and socket connector 210) and the chamber of the mask body 100 may be provided by the extension element 212 having an outer perimeter commensurate with a perimeter wall of the aperture 106 of the mask body 100. In such embodiments, the size and shape of the outer perimeter, of the extension element 212, and the perimeter wall of the aperture 106 are configurable provided that they are sufficiently similar to provide an airtight seal.

The mask frame 200 may be constructed using a thermoplastic polymer. In some embodiments, the thermoplastic polymer may be polypropylene. The mask frame 200 may additionally or alternatively be constructed using one or more rather flexible materials, such as PVC and/or acrylonitrile-butadiene-styrene (ABS). The mask frame 200 may additionally or alternative be construed using one or more malleable metals, which may bend under applied force and retain form adjustments.

Mask Cushion

Figure 3A:
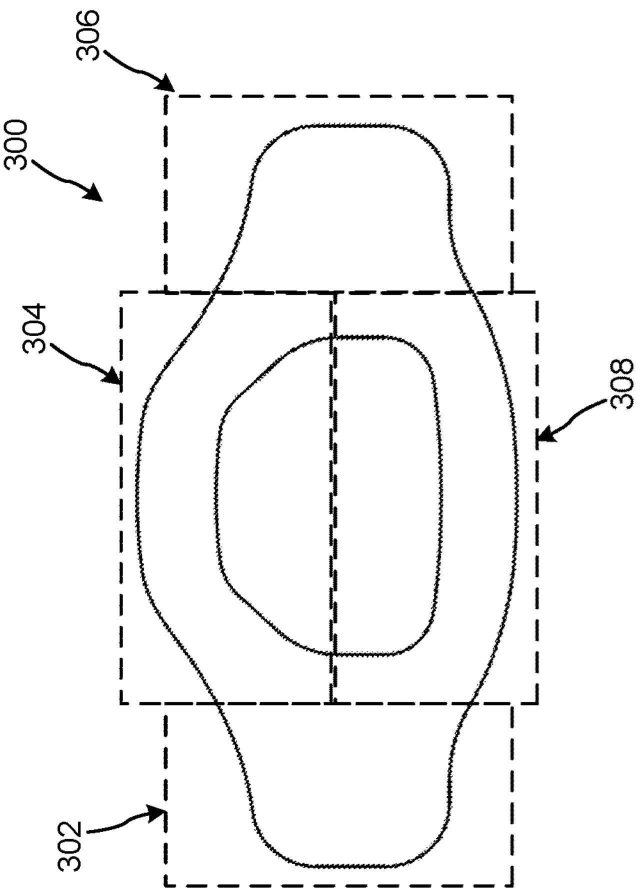
FIG. 3A is a front view of a mask cushion, according to embodiments of the present disclosure.
Figure 3B:
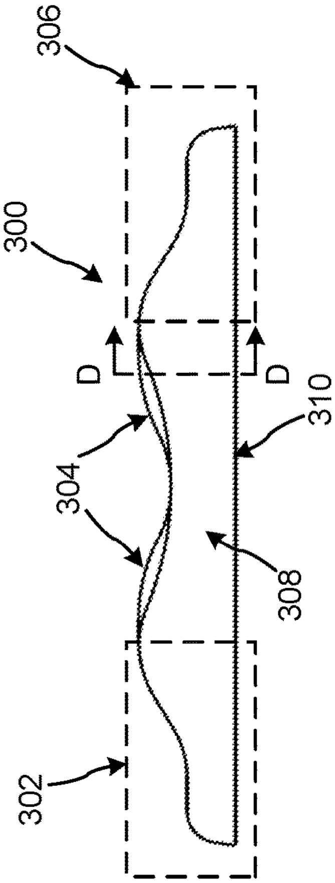
FIG. 3B is a bottom-planar view of the mask cushion of FIG. 3A, according to embodiments of the present disclosure.
Figure 3C:
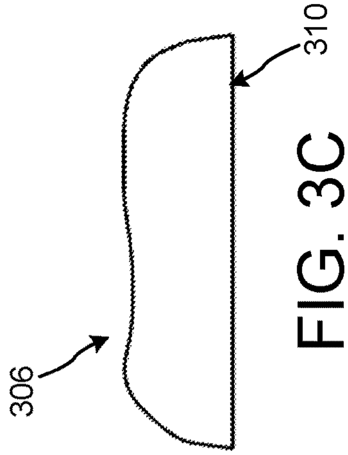
FIG. 3C is a cross-sectional view of the mask cushion of FIG. 3B taken along line D-D, according to embodiments of the present disclosure.
Figure 4C:
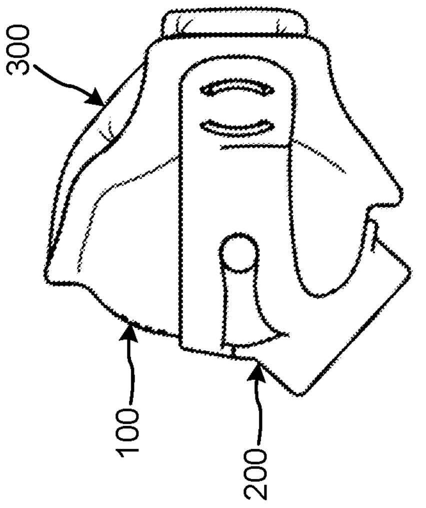
FIG. 4C is a left-side view of the mask assembly of FIG. 4A, according to embodiments of the present disclosure.
Figure 4B:
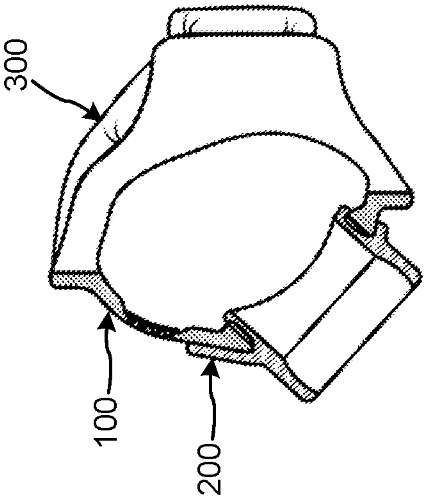
FIG. 4B is a cross-sectional view of the mask assembly of FIG. 4A taken along line E-E, according to embodiments of the present disclosure.
Figure 4A:
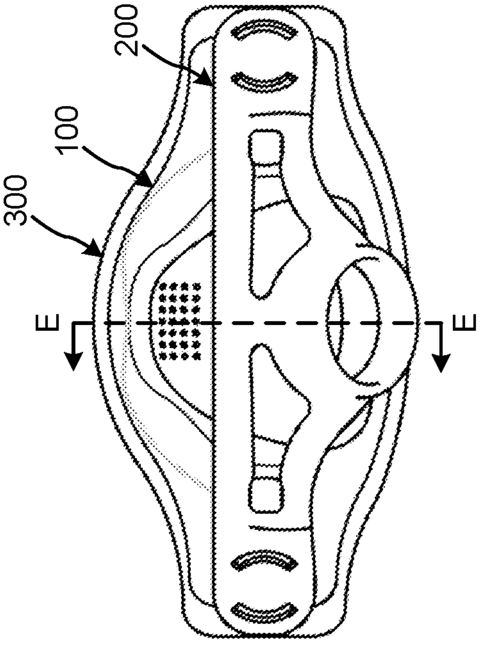
FIG. 4A is a front view of a mask assembly, according to embodiments of the present disclosure.
Figure 4D:
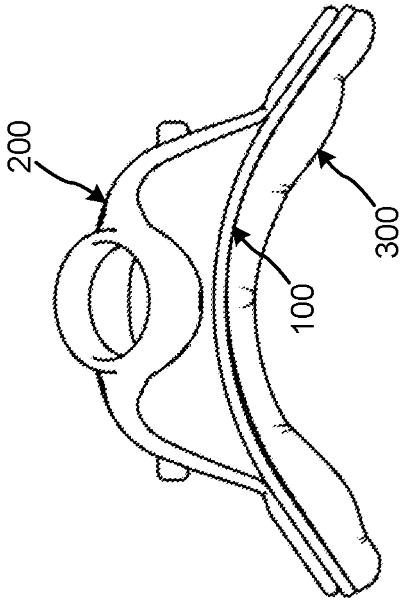
FIG. 4D is a bottom view of the mask assembly of FIG. 4A, according to embodiments of the present disclosure.

FIGS. 3A-3C illustrate an example mask cushion 300 of the present disclosure. The mask cushion 300 may be viewed as including four portions: a first elongated portion 302, an upper portion 304, a second elongated portion 306, and a lower portion 308. The first elongated portion 302 may abut the second elongated portion 112*b*, of the mask body 100, when an attachment face 310, of the mask cushion 300, is permanently or removably affixed to the cushion attachment surface 114 of the mask body 100. Likewise, the second elongated portion 306 may abut the first elongated portion 112*a*, of the mask body 100, when the attachment face 310, of the mask cushion 300, is permanently or removably affixed to the cushion attachment surface 114 of the mask body 100.

In at least some embodiments, the attachment face 310 may be glued to the cushion attachment surface 114 (e.g., using any commercially available or proprietary adhesive). In at least some embodiments, the cushion attachment surface 114, of the mask body 100, may include one or more protrusions (or protruding edges) configured to be inserted within the mask cushion 300 through the attachment face 310, thereby physically and removably coupling the mask cushion 300 to the mask body 100. It thus follows that the mask cushion 300 of the present disclosure is replaceable.

As illustrated in FIG. 3A, the upper portion 304 and the lower portion 308 may each be positioned between the first elongated portion 302 and the second elongated portion 306. The upper portion 304 is configured to contact and create an airtight seal with a nose of a user. When the mask cushion 300 is configured for affixation to a nasal mask body, the lower portion 308 may be configured to contact and create an airtight seal with an upper lip of a user. When the mask cushion 300 is configured for affixation to an oronasal mask body, the lower portion 308 may be configured to contact and create an airtight seal with a chin of a user.

In at least some embodiments, the upper portion 304 and the lower portion 308 may each be configured with at least three primary faces: a skin contact face; the attachment face 310; and a third face. The skin contact face may be the longest face of the faces. In at least some embodiments, the third face may have a length that is less than about 70% to about 90% of the length of the skin contact face. In instances where the upper portion 304 and/or the lower portion 308 are triangular is cross-section, the angle formed between the attachment face 310 and the third face may be between about 70° and about 90°. In at least some embodiments (e.g., for manufacturing reasons), a range of between about 70° and 89° degrees may be preferred.

The third face may occupy an inner perimeter of the mask cushion 300 and the skin contact face may occupy the outer perimeter of the mask cushion 300. In cross-section, the transition between the faces, particularly the transition between the third face and the skin contact face, may be rounded, slightly rounded or even flat. The reason for the rounded or flat nature of the transition may be results of the manufacturing process used to create the mask cushion 300.

In at least some embodiments, the upper portion 304 and/or the lower portion 308 may have more than three primary faces. One skilled in the art will recognize, for example, that a trapezoidal cross-section may be beneficial in at least some instances.

The mask cushion 300 of the present disclosure can be comprised of one or more formed flexible materials having a durometer value of 60 or less on a Type 000 Shore scale; a durometer value of 50 or less on a Type 000 Shore scale; a durometer value of 40 or less on a Type 000 Shore scale; a durometer value of 30 or less on a Type 000 Shore scale; a durometer value of 20 or less on a Type 000 Shore scale; or a durometer value of 10 or less on a Type 000 Shore scale. Example formed flexible materials suitable for use in the mask cushion 300 of the present disclosure are a silicone gel bladder, an air filled bladder, foam (of various types known to one of ordinary skill in the art), and rubber (natural or synthetic, such as liquid silicone rubber).

The Shore durometer is a device known to one of ordinary skill in the art for measuring the hardness of a material, typically of polymers, elastomers, and rubbers. Higher numbers on the scale indicate a greater resistance to indentation and thus harder materials. Lower numbers indicate less resistance and softer materials. The term is also used to describe a material's rating on the scale, as in an object having a "'Shore durometer of 90." Shore durometers are designed to measure specific scale ranges. A Type 000 durometer measures the hardness of very soft materials.

In at least some embodiments, the mask cushion 300 may include an external membrane bladder containing a fluid or gel. The external membrane bladder may be formed from one or more thermopolymer sheets. Thermopolymer sheet material is known to one of ordinary skill in the art. Examples of such materials include sheets comprising urethane, polyurethane, latex, nitrile, and other natural and synthetic polymers. The external membrane bladder may be formed from a sheet of thermopolymer comprising, for example, a first and a second thermopolymer sheet portion. The term "thermopolymer sheet portion" is defined to mean a portion of a single sheet folded or otherwise manipulated to form more than one face of the mask cushion 300.

In some embodiments, silicone gel may be used to fill the external membrane bladder. According to the present disclosure, a mask cushion 300, having an external membrane bladder filled with silicone gel may have a durometer value of 60 or less on a Type 000 Shore scale; a durometer value of 50 or less on a Type 000 Shore scale; a durometer value of 40 or less on a Type 000 Shore scale; a durometer value of 30 or less on a Type 000 Shore scale; a durometer value of 20 or less on a Type 000 Shore scale; or a durometer value of 10 or less on a Type 000 Shore scale. However, it is noted that the present disclosure envisions materials other than silicone gel may be used to fill the external membrane bladder while still maintaining a durometer value of 60 or less on a Type 000 Shore scale.

In some embodiments, the mask cushion 300 of the present disclosure may be configured with a filled external membrane bladder. For example, the mask cushion 300 may be comprised of foam and/or rubber (e.g., liquid silicone rubber) that is molded or otherwise shaped (e.g., by cutting) without the need for an external membrane bladder.

Mask Assembly

Figure 5:
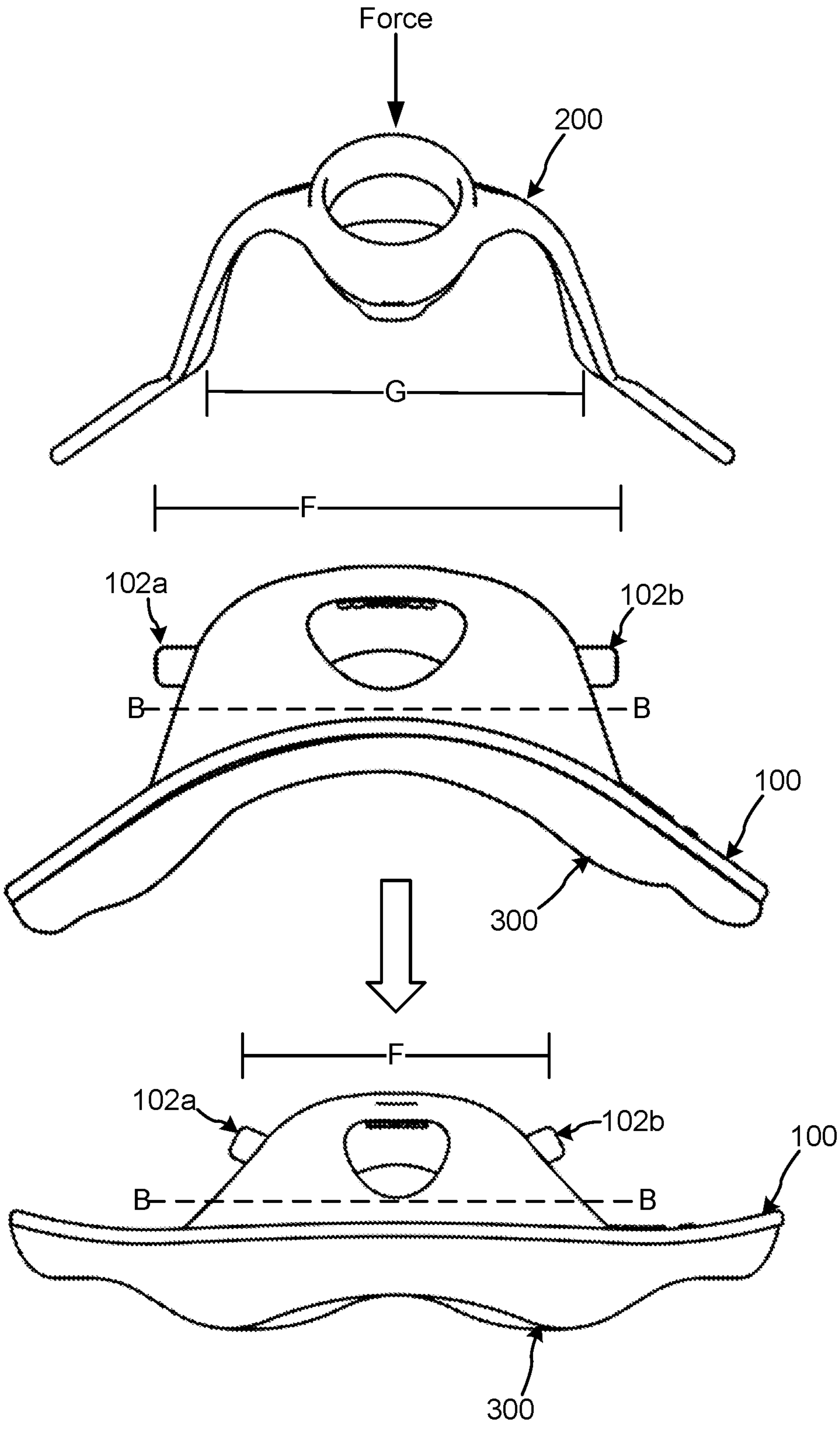
FIG. 5 is a conceptual diagram for coupling the mask body of FIGS. 1A-1D to the mask frame of FIGS. 2D-2D to produce the mask assembly of FIGS. 4A-4D, according to embodiments of the present disclosure.

FIGS. 4A-4D illustrate a mask assembly including the mask body 100 coupled to the mask frame 200. FIG. 5 is a conceptual diagram illustrating how the mask body 100 may be coupled to the mask frame 200, according to embodiments of the present disclosure.

To initiate creation of the mask assembly, the mask body 100 may be placed on a surface (e.g., a table, countertop, etc.) with the mask frame 200 placed on top of the mask body 100 (as illustrated above the arrow in FIG. 5). Once the mask frame 200 is placed on top of the mask body 100, the extension element 212, of the mask frame 200, may be inserted through the aperture 106 of the mask body 100. After the extension element 212 is inserted through the aperture 106, force may be applied to the convex surface 206 of the mask frame 200 (e.g., at or proximate the ball and socket connector 210. As the force is applied, the mask body 100 may flatten out along the plane B-B, resulting in orientations of the first prong 102*a* and the second prong 102*b* changing and a distance F decreasing between the first prong 102*a* and the second prong 102*b* (as illustrated by the two orientations of the mask body 100 in FIG. 5). Additionally or alternatively, application of the force, on the convex surface 206 of the mask frame 200, may result in the mask frame 200 being less arcuate, and as a result a distance G between the first aperture 204*a* and the second aperture 204*b* of the mask frame 200 may increase.

Once the distance F between the first prong 102*a* and the second prong 102*b* is decreased (as shown in the bottom illustrated mask body 100 of FIG. 5), and optionally once the distance G between the first aperture 204*a* and the second aperture 204*b* is increased, the first prong 102*a* and the second prong 102*b* may be oriented to be inserted through the first aperture 204*a* and the second aperture 204*b*, respectively. Once the first prong 102*a* and the second prong 102*b* are inserted through the first aperture 204*a* and the second aperture 204*b*, respectively, the force may cease being applied against the convex surface 206 of the mask frame, resulting in the mask assembly of FIGS. 4A-4D where the first prong 102*a* and the second prong 102*b* act upon the first aperture 204*a* and the second aperture 204*b*, respectively, to connect the mask body 100 to the mask frame 200.

While not illustrated in FIGS. 4A-4D, it will be appreciated that the mask cushion 300 may be affixed to the mask body 100 in the mask assembly. In operation, when a user first puts the mask assembly to the user face, contact of the face may be limited to the upper portion 304 of the mask cushion 300, the lower portion 308 of the mask cushion 300, and limited portions of the first elongated portion 302 and the second elongated portion 306 located at or proximate the chamber of the mask assembly. Once headgear of the mask assembly is positioned, and pressure is applied to the mask frame 200 of the mask assembly, the first elongated portion 112*a* and the second elongated portion 112*b*, of the mask body 100 formed of a flexible material, may fold towards the user's face, resulting in additional surface contact between the user's face and the first elongated portion 302 and the second elongated portion 306 of the mask cushion 300. This increased surface contact, in most if not all circumstances, results in a better airtight seal between the mask cushion 300 and the user's face.

By forming the mask body 100 from a flexible material, the plane B-B of the mask body 100 may remain constant (or relatively constant) during folding of the first elongated portion 112*a* and the second elongated portion 112*b* of the mask body 100. As a result of the plane B-B remaining relatively or completely constant, dimensions of the chamber of the mask body 100 may remain completely or relatively constant. As a result of the dimensions of the chamber remaining completely or relatively constant, the bottom portion of the mask body 100 (corresponding to a user's upper lip for a nasal mask body, and a user's chin for an oronasal mask body) may not deform via "puckering" (i.e., bulging out causing a loss of contact between the lower portion 308 of the mask cushion 300 and the user's face) while the first elongated portion 112*a* and the second elongated portion 112*b* of the mask body 100 are folded due to pulling by the headgear. In at least some embodiments, the first elongated portion 112*a* and the second elongated portion 112*b*, of the mask body 100, may fold inward up to about 50° from a resting orientation, and outward up to about 20° from a resting orientation, without causing the bottom portion of the mask body 100 to pucker. It will thus be appreciated that the teachings herein provide an improved seal between the mask cushion 300 and the user's face.

While the present invention has been particularly described in conjunction with specific embodiments, it is evident that many alternatives, modifications, and variations will be apparent to those skilled in the art in light of the foregoing description. It is therefore contemplated that the appended claims will embrace any such alternatives, modifications, and variations as falling within the true scope and spirit of the present invention.

What is claimed is:

1. A positive airway pressure (PAP) mask assembly comprising:

a mask frame including a concave surface including a first aperture and a second aperture therein, the mask frame further including an extension element extending from the concave surface;

a mask body formed from a polyvinyl chloride, the mask body comprising a convex surface, a first prong and a second prong each extending outwardly from the convex surface, and a third aperture in the convex surface; and a mask cushion coupled to the mask body, the mask cushion comprising a gel, wherein a distance between the first prong and second prong is reduced when a force is applied to the convex surface of the mask body, wherein the first prong and the second prong are configured to be inserted through the first aperture and the second aperture, respectively, when the distance is reduced, wherein the first prong and the second prong are configured to act upon the first aperture and the second aperture, respectively, to removably connect the mask body to the mask frame, and wherein the extension element of the mask frame is configured to be inserted through and provide a seal with the third aperture of the mask body when the first prong and the second prong act upon the first aperture and the second aperture, respectively.

2. The PAP mask assembly of claim 1, wherein the mask frame further includes a socket portion of a ball and socket connector.

3. The PAP mask assembly of claim 1, wherein:

the mask frame further includes a convex surface; and the first prong and the second prong are configured to be inserted through the first aperture and the second aperture, respectively, when a force is applied to the convex surface of the mask frame.

4. The PAP mask assembly of claim 3, wherein a distance between the first aperture and the second aperture is increased when the force is applied to the convex surface of the mask frame.

5. The PAP mask assembly of claim 1, wherein the mask body is configured to fit over at least a portion of a nose of a user.

6. The PAP mask assembly of claim 1, wherein the mask body is configured to fit over a mouth and at least a portion of a nose of a user.

7. The PAP mask assembly of claim 1, wherein the mask body further includes a retaining element therein, the retaining element being configured to reshape and retain the convex surface of the mask body to features of a face of a user.

8. A mask frame for a positive airway pressure (PAP) mask assembly, the mask frame comprising:

a concave surface;

a convex surface a first aperture within the concave surface, the first aperture configured to receive a first prong extending from a convex surface of a mask body;

a second aperture within the concave surface, the second aperture configured to receive a second prong extending from the convex surface of the mask body; and an extension element extending from the concave surface, wherein the mask frame is configured to removably connect to the mask body when the first aperture and the second aperture are acted upon by the first prong and the second prong, respectively, wherein the extension element is configured to be inserted through and provide a seal with a third aperture of the mask body when the first aperture and the second aperture are acted upon by the first prong and the second prong, respectively, wherein the first aperture and the second aperture are configured to receive the first prong and the second prong, respectively, when a force is applied to the convex surface of the mask frame, wherein a distance between the first aperture and the second aperture is increased when the force is applied to the convex surface.

9. The mask frame of claim 8, further comprising a socket portion of a ball and socket connector.

10. The mask frame of claim 8, wherein the mask frame is constructed using a thermoplastic polymer.

11. The mask frame of claim 10, wherein the thermoplastic polymer is polypropylene.

12. The mask frame of claim 8, wherein the mask frame is constructed using polyvinyl chloride.

13. The mask frame of claim 8, wherein the mask frame is constructed using acrylonitrile-butadiene-styrene.

14. The mask frame of claim 8, wherein the mask frame is constructed using at least one malleable metal.

* * * * *